United States Patent [19]

Knutson

[11] 4,187,841
[45] Feb. 12, 1980

[54] BONE COMPRESSION OR DISTRACTION DEVICE

[76] Inventor: Richard A. Knutson, c/o Delta Orthopaedic Clinic, 130 N. Shelby St., P.O. Box 633, Greenville, Miss. 38701

[21] Appl. No.: 922,786

[22] Filed: Jul. 7, 1978

[51] Int. Cl.² ................... A61F 5/04; A61B 17/18
[52] U.S. Cl. .................. 128/92 E; 128/92 A; 128/84 B
[58] Field of Search ......... 128/92 A, 92 B, 92 D, 128/92 E, 92 EA, 92 R, 92 G, 84 R, 84 B, 83

[56] References Cited

U.S. PATENT DOCUMENTS

| | | | |
|---|---|---|---|
| 1,217,637 | 2/1917 | Rink | 128/92 EA |
| 1,920,821 | 8/1933 | Wassenaar | 128/92 EA |
| 2,238,870 | 4/1941 | Haynes | 128/92 A |
| 2,250,417 | 7/1941 | Ettinger | 128/92 A |
| 2,251,209 | 7/1941 | Stader | 128/92 A |
| 3,244,170 | 4/1966 | McElvenny | 128/92 D |
| 3,604,414 | 9/1971 | Borges | 128/92 D |
| 3,709,219 | 1/1973 | Holloran | 128/92 E |
| 3,862,631 | 1/1975 | Austin | 128/92 B |
| 3,900,025 | 8/1975 | Barnés, Jr. | 128/92 D |

FOREIGN PATENT DOCUMENTS 152534  9/1961  U.S.S.R. ................. 128/92 EA

Primary Examiner—Ronald L. Frinks
Attorney, Agent, or Firm—Snider, Sterne & Saidman

[57] ABSTRACT

A surgical tool which may be utilized either for compression or distraction of a fractured bone. The tool includes a threaded shaft having a pair of cap members secured to each end thereof. Projecting from one of the cap members is a short pin which is preferably angled either towards or away from the other cap member. An internally threaded sleeve is mounted on the shaft between the cap members and includes a knob having a knurled outer surface for permitting the sleeve to be manually adjusted in either direction along the threaded shaft. Another pin-supporting member is removably mounted about the sleeve and has another short pin projecting from one surface thereof. The two pins are positioned within pre-drilled holes on each side of a fractured bone that is to be compressed or distracted.

16 Claims, 14 Drawing Figures

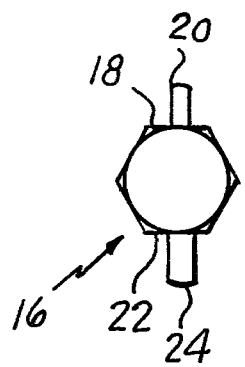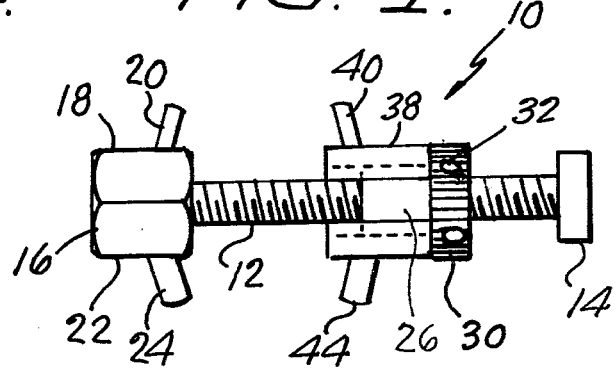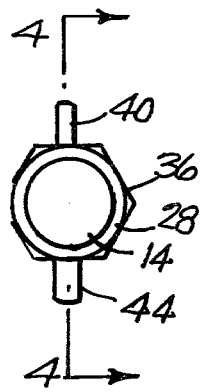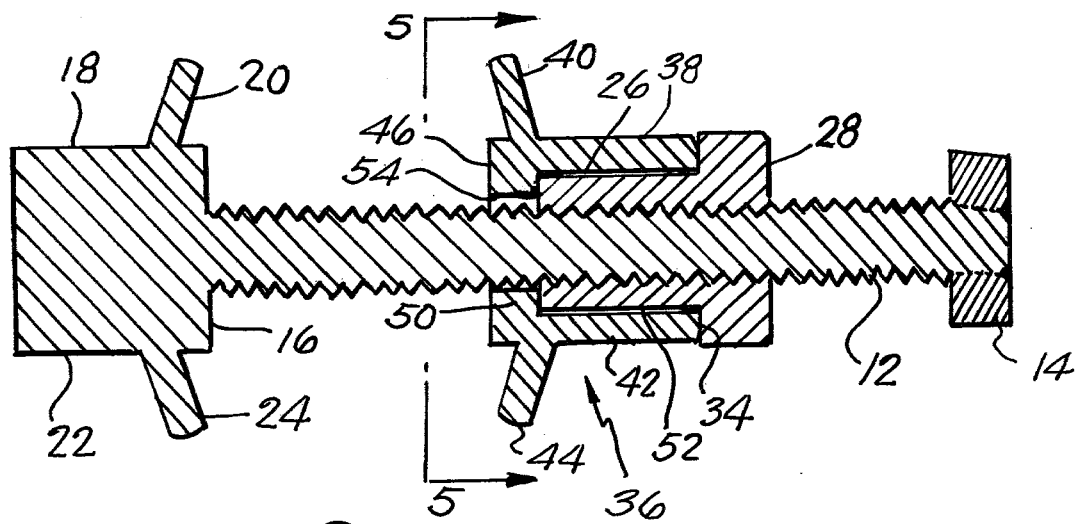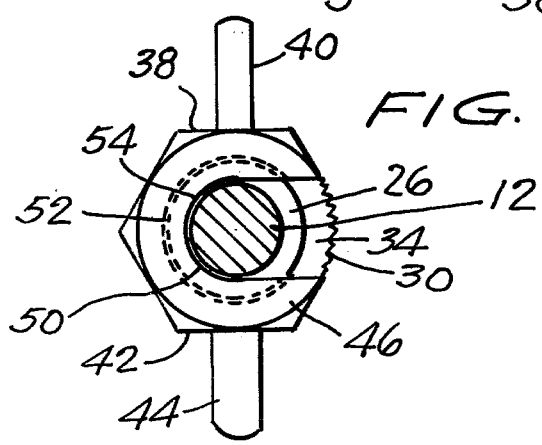

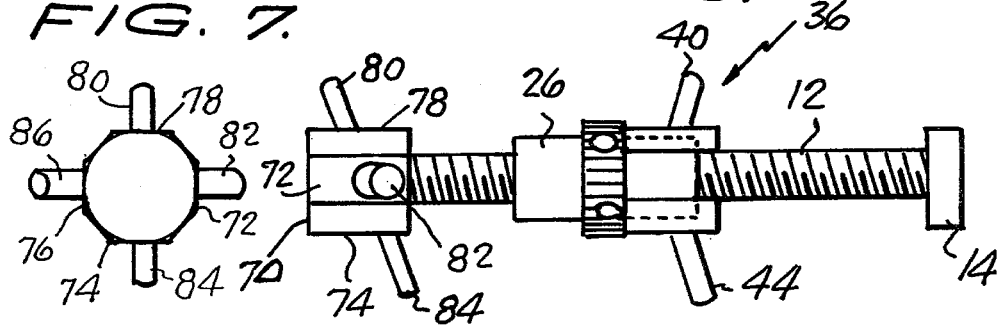
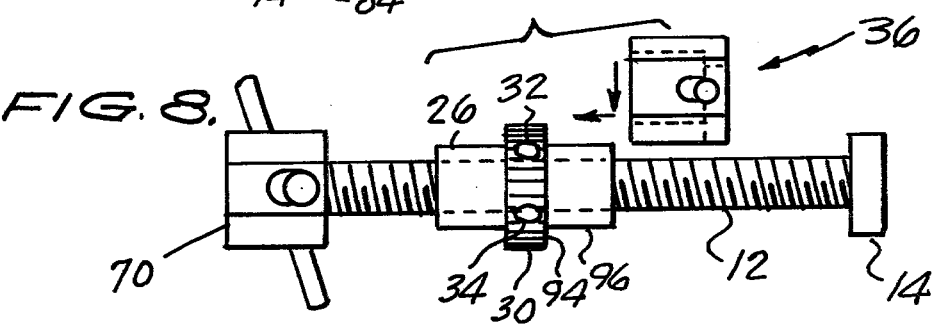
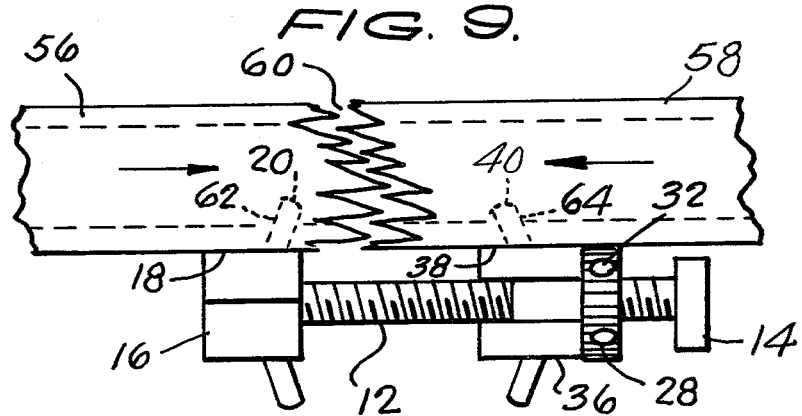
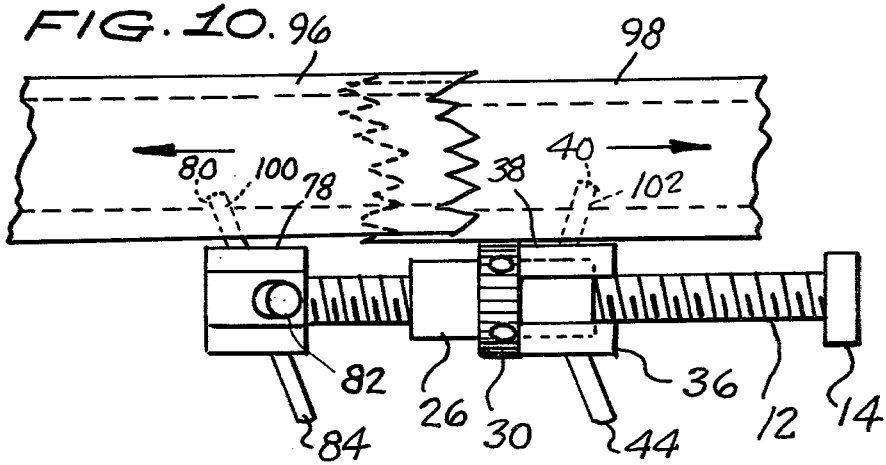

4,187,841

BONE COMPRESSION OR DISTRACTION DEVICE

BACKGROUND OF THE INVENTION

1. Field of the Invention

The present invention is related to surgical tools and, more particularly, is directed towards a device which may be utilized to either compress or distract a bone fracture.

2. Description of Prior Art

Healing of a bone fracture may be enhanced by utilizing various compression devices which hold the fractured bone together. Such devices typically utilize a bone plate which must be secured to the bone on both sides of the fracture by, for example, pins, clamps or screws.

In order to successfully apply such plates, it is necessary to compress the bone, or distract and then compress the bone, depending upon the type of fracture, during surgery. After compression, distraction, or both, the bone must be held immobile while the plate is being installed.

Presently, various bone hooks and clamps are utilized for compression and/or distraction. Some clamps partially encircle both bone portions and then attempt to apply a linear force to compress same. Disadvantages of such bone encircling clamps are that, due to the applied pressure, the bone may break, or the clamp may slip. Further, it is extremely difficult, with the prior art devices, to apply a solid and steady compressive force.

For distraction (removal of overlap), bone hooks, which require the use of two hands, are commonly utilized. Due to their disjunctive nature, such hooks provide uneven, unsteady forces which are difficult to manipulate and control.

Accordingly, it may be appreciated that the prior art bone compression and distraction devices have been difficult to control, generally are complex in construction, require two hands for proper manipulation, do not provide even, steady application of force in the proper direction, require relatively large incisions, and are equally difficult to remove as to install.

Prior art U.S. patents in this general area of which I am aware include: Nos. 1,217,637; 1,920,821; 2,238,870; 2,251,209; 3,244,170; 3,709,219; 3,862,631; and 3,900,025.

OBJECTS AND SUMMARY OF THE INVENTION

It is accordingly a primary object of the present invention to provide a new and improved bone compression and distraction device which overcomes all of the disadvantages noted above with respect to prior art devices.

Another object of the present invention is to provide a surgical device which may be utilized either for bone compression or distraction with equal facility and which does not require encircling of the bone.

Another object of the present invention is to provide a bone compression and distraction device which holds the bone solidly, allows the surgeon to have two hands free, requires minimal assistance in installation and removal, allows free access to other bone surfaces, and which provides even and steady forces in both compression and distraction.

An additional object of the present invention is to provide a unique bone compression and distraction device which is of simple construction, is durable, easy to clean, has no sharp edges, may be utilized on either small or large bones, provides firm bone contact and hold during use, permits easy adjustment during use for precise fit, and includes structural features which prevent misuse.

Another general object of the present invention is to provide an inexpensive bone compression or distraction tool the use of which lessens soft tissue exposure, bone damage, and thereby will reduce potential infection.

The foregoing and other objects are attained in accordance with one aspect of the present invention through the provision of a bone compression or distraction tool which comprises a threaded shaft and a cap member secured to one end of the shaft and having at least one relatively short pin projecting therefrom. The tool also includes a threaded sleeve rotatably engaged about the threaded shaft and knob means secured to and extending outwardly from the sleeve for enabling rotation of same and which forms a shoulder. The tool further includes a pin carrying member which is removably fittable about the sleeve and has at least one relatively short pin projecting therefrom. One end of the pin carrying member is engagable by the shoulder of the knob means so as to move toward or away from the cap member upon rotation of the knob means.

In accordance with other aspects of the present invention, the cap member may include a plurality of differently sized pins projecting therefrom, whereby bones of differing sizes may be worked on by the same tool.

The cap member and the pin carrying member each have at least one substantially planar face which is adapted to be adjacent the bone during use and which are coplanar, parallel to the axis of the shaft, and respectively have the short pins extending therefrom. In a preferred form, each of the short pins are approximately ¼ inch long and are angled at approximately 5° from an axis perpendicular to the axis of the threaded shaft. In one form, the short pins are inclined towards one another, and the threaded sleeve is positioned between the knob means and the cap member, whereby the tool serves as a bone compression device. In another form, the short pins are angled away from one another, and the knob means is positioned between the cap member and the threaded sleeve, whereby the tool serves as a bone distraction device. In a preferred embodiment, the threaded sleeve extends along the shaft on both sides of the knob member whereby the tool may serve as either a bone compression or distraction device, depending upon the positioning of the pin carrying member.

In accordance with other aspects of the present invention, the pin carrying member includes an opening along its length which is wider than the diameter of the shaft but which is smaller than the diameter of the sleeve. The pin carrying member also includes an unthreaded inner substantially cylindrical surface having a smaller radius at one portion thereof than that at a second portion thereof. The first portion of the inner surface is adapted to be placed about the threaded shaft, while the second portion thereof is adapted to be placed about the sleeve. A second cap member is preferably secured to the other end of the shaft, and the knob means may be provided with apertures on the periphery thereof adapted to receive a spanner wrench for assisting in the turning or tightening of same.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 1 is a side view of a preferred embodiment of a bone compression tool in accordance with the present invention;

FIG. 2 is a left-side view of the preferred embodiment illustrated in FIG. 1;

FIG. 3 is a right side view of the preferred embodiment illustrated in FIG. 1;

FIG. 4 is an enlarged, cross-sectional view of the preferred embodiment illustrated in FIGS. 1 through 3 and which is taken along line 4—4 of FIG. 3;

FIG. 5 is a sectional view of the preferred embodiment of FIGS. 1 through 4 which is taken along line 5—5 of FIG. 4;

FIG. 6 is a side view of an alternate preferred embodiment of the present invention;

FIG. 7 is a left end view of the alternate embodiment of FIG. 6;

FIG. 8 is a view similar to FIG. 6 but showing one component of the alternate embodiment removed;

FIG. 9 is a schematic illustration of the first preferred embodiment of FIGS. 1 through 5 in use;

FIG. 10 is a side view which schematically illustrates the operation of the embodiment of FIGS. 6 through 8;

DETAILED DESCRIPTION OF THE PREFERRED EMBODIMENTS

Figure 11:
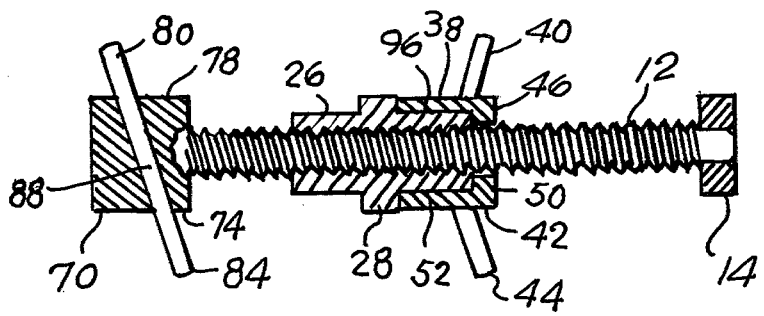
FIG. 11 is a cross-sectional view illustrating the components of the alternate embodiment of FIGS. 6 through 8.

Referring now to the drawings, wherein like reference numerals represent identical or corresponding parts throughout the several views, and more particularly to FIGS. 1 through 5 thereof, reference numeral 10 indicates one preferred embodiment of the present invention which, in this form, is utilized as a bone compression tool.

The bone compression device 10 includes a threaded shaft 12 having a round cap 14 attached to one end thereof. Cap 14 may be secured, for example, by being tapped, threaded and spot-welded to one end of the shaft 12.

Secured to the distal end of the shaft 12 is a fixed cap 16 so that elements 12, 14 and 16 move together as a unit either laterally or in rotation. The fixed cap 16 includes at least one substantially planar surface 18 which is adapted to be positioned adjacent the surface of the bone during use.

Projecting from the planar surface 18 is a relatively short (e.g., ¼ inch) pin 20 which is adapted to be inserted within a predrilled hole in the fractured bone. Pin 20 may be any convenient diameter, such as ⅛ inch, and is preferably angled at approximately a 5° angle with respect to the vertical axis perpendicular to the axis of shaft 12.

The compression device 10 of the present invention may be provided with more than one pin for added versatility. For example, on the bottom of the fixed cap 16 may be provided an additional planar surface 22 having a larger diameter (e.g., 3/16 inch) pin 24 projecting therefrom.

As seen clearly in FIG. 2, the fixed cap 16 is provided in this embodiment with a hexagonal outer surface, although the precise shape thereof may be varied to suit the particular need.

Figure 14:
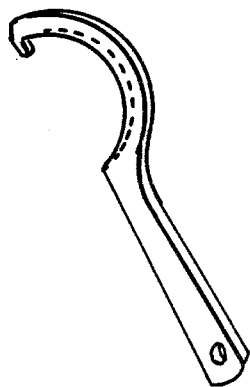
FIG. 14 is a perspective view of a spanner wrench which may be utilized with either of the preferred embodiments of the present invention.

Positioned between the end caps 14 and 16 is a sleeve 26 which is internally threaded so as to be movable along the length of threaded shaft 12. A knob 28 is formed at one end of the sleeve 26 and cannot accidently be rotated off shaft 12 due to end cap 14. Knob 28 preferably has a knurled outer surface 30 to facilitate manual grasping and turning thereof, thereby preventing slippage during surgical use due to blood and other tissue fluids. The outer surface 30 also preferably includes a plurality of apertures 32 which are spaced to receive a turning tool, such as the spanner wrench illustrated, for example, in FIG. 14, allowing for more firm compression than attainable through digital rotation of knob 28.

The junction between sleeve 26 and the knob 28 forms a shoulder 34 for applying a compressive force to a removable pin-carrying member indicated generally by reference numeral 36. Member 36 includes at least one planar surface 38 which is preferably coplanar with the planar surface 18 of fixed cap 16. Extending from planar surface 38 is a relatively short pin 40 of the same diameter and length as the pin 20, but which is angled towards pin 20. The pin-carrying member 36 also preferably includes an additional planar surface 42 having a larger diameter pin 44 extending therefrom. Pin 44 is sized similarly to pin 24, and surface 42 is preferably coplanar with surface 22.

Figure 13:
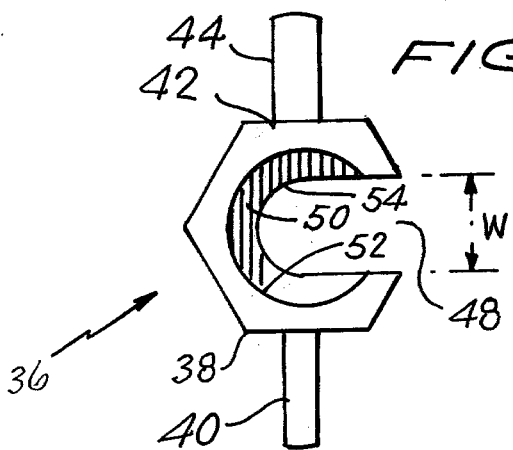
FIG. 13 is an enlarged view of one of the components common to both of the preferred embodiments of the present invention.

Referring now principally to FIGS. 5 and 13, the removable pin-carrying member 36 includes an end portion 46 having a C-shaped opening 48. Opening 48 extends along the entire length of member 36 and is of a width W which is smaller than the diameter of threaded sleeve 26 but has a slightly larger diameter than that of the threaded shaft 12.

The inner surface of the member 36 is unthreaded and substantially cylindrical (except for opening 48) and forms a reduced diameter portion 50 which is adapted to fit about the shaft 12, and an increased diameter portion 52 which is adapted to fit about the sleeve 26. Note that the portion 54 of the opening 48 that is adjacent the shaft 12 is also unthreaded so that the member 36 may be pushed towards the fixed member 16 by rotation of knob 28 without itself being rotated.

In operation of the first embodiment, referring to FIG. 9, there are illustrated two bone portions 56 and 58 separated by a fracture 60. Appropriately-sized holes 62 and 64 are drilled through the cortex of bone portions 56 and 58. After member 36 is positioned about shaft 12, pin 20 is inserted into hole 62 until surface 18 is adjacent the outer surface of bone 56 adjacent hole 62. Knob 28 is then rotated until pin 40 is properly positioned to fit within hole 64. When pin 40 is properly seated in hole 64, as evidenced by surface 38 being adjacent bone 58, any adjustment to the position of pin 20 may be effected by rotating knob 14. When both pins are properly seated, the knob 28 may be rotated either manually or with the assistance of the spanner wrench (FIG. 14) to draw the bone portions 56 and 58 into compression. Afer proper compression, the tool 10 of the present invention remains in position while an appropriate bone plate is secured. The non-encircling nature of the tool 10 facilitates installation of the bone plate, and the secure seating of pins 20 and 40, combined with the adjacent planar faces 18 and 38, free the hands of the surgeon to install the plate without fear of additional fracture, or loosening of the present invention. After the bone plate (not shown) is secured, the tool 10 of the present invention may be readily removed by simply loosening the knob 28.

Note that by virtue of the dual diameters of the pin-carrying member 36, it is impossible for same to fall off the sleeve 26 during the procedure. That is to say, in order to be removed from sleeve 26, the member 36 must be axially moved along shaft 12 until the increased diameter portion 52 is free of the sleeve 26, whereupon the opening 48 will allow member 36 to be removed from the shaft.

Referring now to FIGS. 6, 7, 8, 11 and 12, there is illustrated an alternative embodiment of the present invention which is particularly versatile in that either bone compression or distraction may be effectuated with a single tool. The same pin-carrying removable member 36 may be utilized for this embodiment as with the first embodiment. However, for bone distraction, additional pins are necessary in the fixed end piece 70 which are angled away from the threaded sleeve portion of the device. For example, the fixed end piece 70 includes several planar surfaces 72, 74, 76 and 78 each of which has a relatively short pin 80, 82, 84 and 86 extending therefrom. Pins 80 and 84 may be similarly sized (e.g., ⅛ inch) and may, as best illustrated in FIG. 11, consists of the same piece 88 rigidly fixed within the body 70. Similarly, pins 82 and 86 are of a larger size (e.g., 3/16 inch) and may also consist of the same piece firmly secured within the fixed end 70.

Pins 80 and 86 are angled rearwardly so as to be utilized in a distraction procedure, while pins 82 and 84 are angled forwardly and may be utilized during a compression procedure.

The threaded sleeve portion of this embodiment is modified to include an additional sleeve member 96 which extends to the other side of knurled knob 30 so as to form a shoulder portion 94. Sleeve portion 96 and shoulder 94 are utilized in conjunction with member 36 during a distraction procedure. A cross section of the alternate embodiment illustrating member 36 properly positioned prior to a distraction procedure is illustrated in FIG. 11. It may be appreciated that the similarly sized pins 40 and 80 are angled away from one another. In operation, as illustrated in FIG. 10, bone pieces 96 and 98 overlap and must be distracted by applying forces thereto in a direction opposite to that required for a compression procedure. To this end, appropriately sized holes 100 and 102 are drilled in bone pieces 96 and 98 for receiving pins 80 and 40, respectively. Thereafter, knob 30 is rotated in the opposite sense to the direction it would be rotated for a compression procedure, which draws the bone pieces 96 and 98 away from one another along the direction indicated by the arrows. When the bone pieces 96 and 98 have been sufficiently distracted, additional holes may be drilled and a compression device installed to compress and then apply a plate to the fracture, similar to the procedure described above in connection with FIG. 9.

Figure 12:
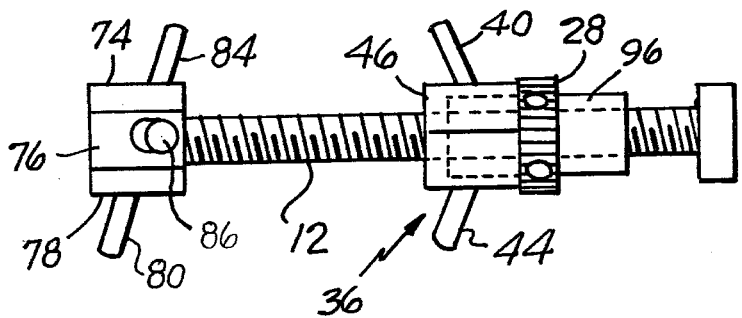
FIG. 12 illustrates the alternate embodiment of FIGS. 6 through 8 and 11 but in an alternate mode of operation.

The versatility of the alternate embodiment is illustrated in FIG. 12, wherein the member 36 is shown placed above sleeve 26 so that pin 40 can cooperate with pin 84 in a compression operation. In such a technique, knob 28 will be rotated in the opposite sense to that utilized in conjunction with a distraction procedure.

In both embodiments of the present invention, the tool consists of three basic pieces; one which is fixed, one which moves, and one which is removable. All pieces are preferably constructed out of stainless steel, to facilitate cleaning and sterilization. The few moving parts and simplicity in construction minimize buildup of foreign material and thereby facilitate use, cleaning, and proper sterilization. The various sizes of pins permit use of the same tool on both large and small bones. The planar surfaces adjacent the projections allow the device to lay flat against a bone during use which adds further to the steady, even application of force. The preferred 5° angle of inclination of the pins provides for firm bone contact and grip during use. The knurled wheel may be rotated by fingertip or by a spanner wrench, as may be necessary. The sleeve prevents the removable piece from falling off during a procedure, and the reduced diameter portion prevents misinstallation of the pin-carrying member.

The present invention may be utilized with a smaller incision than heretofore necessary, allows compression or distraction of the bone with minimal equipment, frees the hands of the surgeon to apply other fixation devices, and holds the bone firmly in proper position without encircling same until removed. Chances of soft tissure exposure and bone damage are minimized, thereby resulting in potentially less infection.

Obviously, numerous modifications and variations of the present invention are possible in light of the above teachings. It is clear, for example, that a tool for performing bone distraction only could be fashioned from the second embodiment, which would be similar to the first embodiment. Further, different shapes of projections could be added to or substituted for the short pins. For example, a cupped spoon-shaped projection could be added to the fixed and moving components described above, thereby providing similar compression and distraction forces on ribs, especially during thoracic or scoliosis surgery. Therefore, I wish it to be understood that within the scope of the appended claims the invention may be practiced otherwise than as specifically described herein.

I claim as my invention:

1. A bone compression or distraction tool, which comprises:
   a threaded shaft;
   a cap member secured to one end of said shaft, said cap member having at least one relatively short pin projecting therefrom;
   a threaded sleeve rotatably engaged about said threaded shaft;
   a knob means secured to and extending outwardly from said sleeve for enabling rotation of same and forming a shoulder; and
   a pin carrying member removably fittable about said sleeve and having at least one relatively short pin projecting therefrom, one end of said pin carrying member being engagable by said shoulder so as to move towards or away from said cap member upon rotation of said knob means.

2. The bone compression or distraction tool as set forth in claim 1, wherein said cap member includes a plurality of pins projecting therefrom.

3. The bone compression or distraction tool as set forth in claim 1, wherein said cap member and said pin carrying member each have at least one substantially planar face adapted to be adjacent the bone and which are coplanar, parallel to the axis of said shaft, and respectively have said short pins extending therefrom.

4. The bone compression or distraction tool as set forth in claim 1, wherein each of said short pins are angled at approximately 5° from an axis perpendicular to the axis of said shaft.

5. The bone compression or distraction tool as set forth in claim 4, wherein said short pins are inclined towards one another whereby said tool serves as a bone compression device.

6. The bone compression or distraction tool as set forth in claim 4, wherein said short pins are inclined away from one another whereby said tool serves as a bone distraction device.

7. The bone compression or distraction tool as set forth in claim 2, wherein certain of said pins have a diameter different than the diameter of other pins whereby bones of differing sizes may be worked on by the same tool.

8. The bone compression or distraction tool as set forth in claim 1, wherein said threaded sleeve is between said knob means and said cap member whereby said tool serves as a bone compression device.

9. The bone compression or distraction tool as set forth in claim 1, wherein said knob means is positioned between said cap member and said threaded sleeve whereby said tool serves as a bone distraction device.

10. The bone compression or distraction tool as set forth in claim 1, wherein said threaded sleeve extends along said shaft on both sides of said knob member whereby said tool serves as either a bone compression or distraction device.

11. The bone compression or distraction tool as set forth in claim 1, wherein said pin carrying member includes an opening along its length which is wider than the diameter of said shaft but smaller than the diameter of said sleeve.

12. The bone compression or distraction tool as set forth in claim 11, wherein said pin carrying member also includes an unthreaded, inner substantially cylindrical surface having a smaller radius at one portion thereof than that at a second portion thereof.

13. The bone compression or distraction tool as set forth in claim 12, wherein said one portion of said inner surface is adapted to be placed about said shaft, while said second portion thereof is adapted to be placed about said sleeve.

14. The bone compression or distraction tool as set forth in claim 7, wherein some of said plurality of pins in said cap member are inclined towards said sleeve, while others of said plurality of pins in said cap member are inclined away from said sleeve.

15. The bone compression or distraction tool as set forth in claim 1, wherein said knob means includes aperture means on the periphery thereof adapted to receive a wrench for turning same.

16. The bone compression or distraction tool as set forth in claim 1, further comprising a second cap member secured to the other end of said shaft.

* * * * *